(12) United States Patent
Joshghani

(10) Patent No.: US 11,617,401 B2
(45) Date of Patent: Apr. 4, 2023

(54) PROTECTIVE DEVICE FOR HUMAN JOINT

(71) Applicants: UNIVERSITEIT GENT, Ghent (BE); Ashkan Mohammad Hassan Joshghani, Ghent (BE)

(72) Inventor: Ashkan Mohammad Hassan Joshghani, Ghent (BE)

(*) Notice: Subject to any disclaimer, the term of this patent is extended or adjusted under 35 U.S.C. 154(b) by 142 days.

(21) Appl. No.: 16/485,896

(22) PCT Filed: Feb. 23, 2018

(86) PCT No.: PCT/EP2018/054541
§ 371 (c)(1),
(2) Date: Aug. 14, 2019

(87) PCT Pub. No.: WO2018/154062
PCT Pub. Date: Aug. 30, 2018

(65) Prior Publication Data
US 2020/0054082 A1 Feb. 20, 2020

(30) Foreign Application Priority Data
Feb. 23, 2017 (EP) ..................................... 17157653

(51) Int. Cl.
*A41D 13/08* (2006.01)
*A41D 19/015* (2006.01)
(Continued)

(52) U.S. Cl.
CPC ..... *A41D 13/087* (2013.01); *A41D 19/01523* (2013.01); *A41D 19/01582* (2013.01);
(Continued)

(58) Field of Classification Search
CPC ............ A41D 13/087; A41D 19/01523; A41D 19/01582; F41B 5/1473; A61F 5/013; A61F 5/10
(Continued)

(56) References Cited

U.S. PATENT DOCUMENTS 1,716,221 A * 6/1929 Fernie .................. A63B 71/146
2/166
2,344,080 A * 3/1944 Burgett .................. A41D 19/00
2/161.2
(Continued)

FOREIGN PATENT DOCUMENTS

CN 1870954 A 11/2006
CN 201360580 Y 12/2009
(Continued)

OTHER PUBLICATIONS

Office Action from corresponding CN application No. 201880013499. 6, dated Mar. 11, 2021.
(Continued)

*Primary Examiner* — Alissa L Hoey
(74) *Attorney, Agent, or Firm* — Workman Nydegger

(57) ABSTRACT

A protective device for protecting a proximal interphalangeal joint and a distal interphalangeal joint of a human finger comprises a flexible sheath for wearing around the human finger and at least four motion constraining elements integrated in or secured to the flexible sheath. The motion constraining element is adapted for constraining a lateral and/or rotational deviation motion of a first phalanx with respect to a second phalanx. The motion constraining element covers a lateral side of the flexible sheath at a location corresponding to the joint and is adapted for resisting elongation of the motion constraining element in a longitudinal direction of the flexible sheath. The motion constraining element is bendable in a direction to allow flexion of the joint. The motion constraining elements for the distal interphalangeal joint and for the proximal interphalangeal joint are distinct and separate elements having different points of engagement on the flexible sheath.

13 Claims, 6 Drawing Sheets

(51) Int. Cl.
*A61F 5/01* (2006.01)
*A61F 5/10* (2006.01)
(52) U.S. Cl.
CPC ............... *A61F 5/013* (2013.01); *A61F 5/10* (2013.01); *A63B 2243/007* (2013.01); *A63B 2243/0037* (2013.01); *A63B 2244/10* (2013.01)
(58) Field of Classification Search
USPC .......................................................... 2/21
See application file for complete search history.

(56) References Cited

U.S. PATENT DOCUMENTS

| | | | | |
|---|---|---|---|---|
| 4,570,269 | A * | 2/1986 | Berlese | A41D 19/01523 2/16 |
| 4,843,651 | A * | 7/1989 | Gramza | A63B 71/148 2/161.1 |
| 4,905,321 | A * | 3/1990 | Walunga | A41D 19/01582 2/160 |
| 5,512,039 | A | 4/1996 | White | |
| 5,517,694 | A * | 5/1996 | Fabry | A41D 19/01582 2/161.1 |
| 5,790,980 | A * | 8/1998 | Yewer, Jr. | A41D 19/01523 2/161.1 |
| 6,279,163 | B1 * | 8/2001 | Hale | A63B 21/065 2/160 |
| 6,651,255 | B1 * | 11/2003 | Schild | A41D 19/015 2/160 |
| 6,839,905 | B1 * | 1/2005 | Bruder | A41D 13/087 2/21 |
| 7,000,256 | B2 | 2/2006 | Kleinert | |
| 8,925,113 | B2 * | 1/2015 | Fricke | A63B 71/141 2/16 |
| 9,241,520 | B2 * | 1/2016 | Curl | A63B 71/141 |
| 9,301,867 | B2 | 4/2016 | Hegland | |
| 9,572,383 | B2 * | 2/2017 | Kleinert | A63B 71/141 |
| 2003/0005506 | A1 * | 1/2003 | Litke | A63B 71/143 2/161.2 |
| 2004/0045071 | A1 * | 3/2004 | Robins | A41D 13/087 2/21 |
| 2004/0103465 | A1 | 6/2004 | Kleinert | |
| 2005/0124464 | A1 | 6/2005 | Priore | |
| 2007/0028357 | A1 * | 2/2007 | Adams, Jr. | A63B 23/16 2/163 |
| 2008/0072358 | A1 | 3/2008 | Kleinert | |
| 2008/0271219 | A1 | 11/2008 | Homer | |
| 2009/0144880 | A1 * | 6/2009 | Desjardin | A63B 71/146 2/161.1 |
| 2012/0030856 | A1 * | 2/2012 | Bevier | A63B 71/148 2/161.1 |
| 2012/0204321 | A1 | 8/2012 | Connelly et al. | |
| 2012/0297515 | A1 * | 11/2012 | Mysyk | A41D 13/087 2/21 |
| 2013/0111642 | A1 * | 5/2013 | Eugene | A63B 71/148 2/21 |
| 2014/0304886 | A1 * | 10/2014 | Eugene | A63B 71/14 2/163 |
| 2015/0251076 | A1 * | 9/2015 | Staton | A41D 13/087 2/161.1 |
| 2017/0239553 | A1 * | 8/2017 | Kowalsky | A41D 19/01582 |

FOREIGN PATENT DOCUMENTS

| | | |
|---|---|---|
| FR | 2910820 A1 | 7/2008 |
| JP | 4055099 B2 | 3/2008 |
| JP | 2015177941 A | 10/2015 |

OTHER PUBLICATIONS

European Search Report from EP Application No. 17157653, dated Aug. 3, 2017.
International Search Report from PCT Application No. PCT/EP2018/054541, dated Apr. 20, 2018.
Office Action from corresponding Japanese Application No. JP2019-546880, dated Nov. 24, 2021.

* cited by examiner

PROTECTIVE DEVICE FOR HUMAN JOINT

FIELD OF THE INVENTION

The invention relates to the field of prosthetic devices, braces and similar protective gear for protecting interphalangeal joints of the human body. More specifically it relates to a protective device for protecting a human joint for articulating a first bone with respect to a second bone, e.g. a human hinge joint, such as an elbow, a knee, an ankle or a digit joint.

BACKGROUND OF THE INVENTION

In the human body, collateral ligament injuries, e.g. radial and ulnar collateral ligament injuries, can occur due to forced lateral deviation and/or rotational movement that is not congruent with the normal range of motion of a joint, e.g. of the finger. For example, ulnar collateral ligament injuries of the thumb are particularly common, and may be referred to as skier's or gamekeeper's thumb, e.g. which may be caused by an abrupt forced radial deviation.

Injuries to the hand are common among athletes, because the hands frequently absorb impact during sports activity. These sports-related injuries may include damage to the supporting ligaments, tendons and/or bones.

Some sports have a notable higher frequency of wrist and finger injuries, for example wrestling or combat sports in which a training suit is used, e.g. a kimono, such as Brazilian Jiu-Jitsu, Judo and Budokai-do. In practicing this type of combat sports, an injury can easily result from a wrong grip. Other sport activities with a high risk of hand injuries may include, for example, climbing, basketball and American football.

Such injuries can be classified into two main categories: traumatic (acute) and overuse (chronic). Nonetheless, the majority of hand injuries, depending on the type of injured tissue, may require a long time to heal, e.g. particularly in the case of torn or ruptured ligaments.

Furthermore, athletes may often be prone to not respecting the proper recovery time and may proceed with training notwithstanding the suffered injuries. Such mentality may be one of the decisive reasons, alongside lower quality of the healed scar tissue in ligaments and tendons, e.g. weakness in tissue strength and tissue stiffness, why an acute injury can develop into a chronic injury.

Repetitive injuries to the ligaments cause improper motion of the joint and play a crucial role in the development of osteo-arthritis (OA). OA is characterized with cartilage loss and reactive new bone formation at joint margins which results in permanent disabilities of the fingers.

It is known in the art to protect joints, e.g. to provide protection against traumatic finger injuries, by using sports tape. Athletic taping can be adopted as a measure to prevent injuries or during post-injury rehabilitation. However, this has the disadvantage that such taping can be expensive, e.g. particularly when required frequently, the application of such taping can be time-consuming and the incorrect application of tape, e.g. by people unskilled in its use, can expose the athlete to injury. Furthermore, taping disadvantageously only provides temporary support, e.g. due to activity and motion the stiffness of the tape may reduce. Taping may also carry a risk due to blood flow restriction caused by the tape when applied too firmly, e.g. in an effort to compensate for the previously mentioned disadvantage.

SUMMARY OF THE INVENTION

It is an object of embodiments of the present invention to provide good and efficient protection against injury of at least one human joint.

The above objective is accomplished by a method and device according to the present invention.

It is an advantage of embodiments of the present invention that a disadvantage of protective taping as known in the prior art, e.g. as mentioned hereinabove, may be overcome.

In a first aspect, the present invention relates to a protective device for protecting a human joint for articulating a first bone with respect to a second bone, e.g. a human hinge joint, such as a digit joint. Particularly, the protective device in accordance with embodiments of the first aspect of the present invention is a protective device for protecting a proximal interphalangeal joint and a distal interphalangeal joint of a human finger.

The protective device comprises a flexible sheath adapted for wearing around the human finger, e.g. around the human joint.

The flexible sheath comprises a palmar side for covering a palmar face of the human finger, a dorsal side for covering a dorsal face of the human finger and two lateral sides for covering respectively an ulnar and a radial face of the human finger.

The protective device also comprises at least four motion constraining elements integrated in or secured to the flexible sheath. The at least four motion constraining elements correspond to respectively each of both lateral sides of each of the proximal interphalangeal joint and the distal interphalangeal joint of the human finger.

Each of the at least four motion constraining elements is adapted for constraining, when the flexible sheath is worn around the human finger, a lateral and/or rotational deviation motion of a first phalanx with respect to a second phalanx articulated with respect to each other by the interphalangeal joint (i.e. a lateral and/or rotational deviation motion of any of the pair of phalanges that are directly connected to the proximal or distal interphalangeal joint to which the motion constraining element corresponds). Thus, each motion constraining element is adapted for constraining, when the flexible sheath is worn, a lateral and/or rotational deviation motion of the first bone with respect to the second bone, e.g. to protect the human joint articulating the first bone with respect to the second bone.

Each of the at least four motion constraining elements covers a lateral side of the flexible sheath at a location corresponding to the interphalangeal joint (i.e. that distal or proximal interphalangeal joint to which the motion constraining element corresponds), when the flexible sheath is worn around the human finger.

Each of the motion constraining elements is adapted for resisting elongation of the motion constraining element in a longitudinal direction of the flexible sheath.

Each of the motion constraining elements is bendable in a dorso-palmar direction to allow flexion of the interphalangeal joint when the flexible sheath is worn around the human finger.

Each of the two motion constraining elements (of the at least four motion constraining elements) that corresponds to the distal interphalangeal joint and each of the two motion constraining elements (of the at least four motion constraining elements) that corresponds to the proximal interphalangeal joint are distinct and separate elements having different points of engagement on the flexible sheath, e.g. such that the former motion constraining element corresponding to the distal joint and the latter motion constraining element corresponding to the proximal joint do not share any common point of engagement on the flexible sheath. For example, a motion constraining element corresponding to the distal interphalangeal joint does not form a continuous structure with a motion constraining element corresponding to the proximal interphalangeal joint. For example, a motion constraining element corresponding to the distal interphalangeal joint is not fixed to the flexible sheath in a point where also a motion constraining element corresponding to the proximal interphalangeal joint is fixed to the flexible sheath.

The flexible sheath may be structure for enveloping the human finger in a close-fitting manner. The flexible sheath may be adapted to exert a compressive force on the human finger when the flexible sheath is worn around the human finger.

For example, the compressive force on the finger may advantageously increase friction between the flexible sheath and the finger when worn, such that the motion constraining elements remain aligned with their corresponding joints in use and such that the motion constraining elements remain sufficiently stationary in at least two end regions thereof to constrain the lateral and/or rotational deviation motion.

The sheath may be a tubular structure. Particularly, the sheath may enclose at least part of the human finger, around the entire cross-sectional circumference of the member on both sides of the joint, e.g. may enclose the member around the first phalanx around its entire circumference and may enclose the member around the second phalanx around its entire circumference, both enclosing parts for enclosing respectively the first phalanx and the second phalanx being connected. However, the sheath is not necessarily continuous over its entire surface area, e.g. may comprise holes, insofar a continuous and closed path is formed around the entire member, e.g. such as to exert a compressive force on the finger, on both sides of the joint. For example, the flexible sheath may comprise or even consist of at least two annular elastic structures for exerting a compressive force on the human body around the shaft of respectively the first phalanx and the second phalanx, when worn around the human finger, and the motion constraining element may be secured to the at least two annular elastic structures, thus forming a connection between the enclosing parts for enclosing respectively the first phalanx and the second phalanx. However, preferably, the sheath may also comprise a flexible textile connecting such annular elastic structures to aid in applying the protective device on the body, aligning the protective device to the anatomical features of the body when worn and to increase comfort when worn.

The deviation motion may refer to a motion, e.g. a lateral or rotational deviation motion, that is unsupported by the natural range of motion of the joint, e.g. causing a displacement of the first phalanx with respect to the second phalanx in a lateral direction, e.g. having a substantial component parallel to a hinge axis of the joint, and/or causing a rotation of the first bone with respect to the second bone along a rotation axis that has a substantial component perpendicular to the hinge axis of the joint.

It is an advantage of embodiments of the present invention that a protection against collateral ligament injuries of the human joint due to lateral deviation and/or rotational deviation is provided without substantially impeding or restricting the natural range of motion of the joint.

In embodiments according to the present invention, the protective device may comprise two of the motion constraining elements respectively covering each lateral side of the flexible sheath at opposite lateral locations of the human joint, when the flexible sheath is worn around the human joint. Thus, two of the motion constraining elements may respectively cover each lateral side of the flexible sheath at opposite lateral locations of the proximal interphalangeal human joint, and (another) two of the motion constraining elements may respectively cover each lateral side of the flexible sheath at opposite lateral locations of the distal interphalangeal joint, when the flexible sheath is worn around the human finger.

In embodiments according to the present invention, each motion constraining element may be secured, e.g. at a first end of the motion constraining element, to the flexible sheath in a first region corresponding to a position of the shaft of the first phalanx and the motion constraining element may be secured, e.g. at a second end of the motion constraining element, to the flexible sheath in a second region corresponding to a position of the shaft of the second phalanx, when the flexible sheath is worn around the human finger.

In embodiments according to the present invention, the flexible sheath may be adapted for exerting a compressive force on the human finger, when worn around the human finger.

In embodiments according to the present invention, the flexible sheath may comprise at least two annular elastic structures for exerting a compressive force on the human body around the shaft of respectively the first phalanx and the second phalanx, when worn around the human joint, and the motion constraining element may be secured to the at least two annular elastic structures.

It is an advantage of embodiments of the present invention that a compressive force can be exerted on the central part of the bones to support the internal anatomical structure. It is an advantage of embodiments of the present invention that annular elastic structures can be provided over the central part of the bones to improve grip. It is an advantage of embodiments of the present invention that annular elastic structures may be provided to securely hold a motion constraining element in an aligned position with respect to a human joint. It is a further advantage of providing the annular elastic structures around the shaft of the bones, in accordance with embodiments of the present invention, that longitudinal displacement of the annular structures and/or of the motion constraining element secured by the annular structures is prevented, e.g. due to a narrow cross section of the human member at the shaft of the bones.

In embodiments according to the present invention, each motion constraining element may comprise at least two elongate elements fastened to or integrated in the flexible sheath, wherein the at least two elongate elements intersect to form a cross where an axis of rotation of the interphalangeal joint intersects the flexible sheath, when worn on the human joint, e.g. to form a cross at a point where an imaginary axis, perpendicular to the plane of motion in which the articulation motion of the joint occurs, projects through the pivot point of the joint. Where reference is made to a 'cross', this is not necessarily limited to two crossing elements, but this may also refer to any number of elements, such as three, intersecting in substantially a same point.

In embodiments of the present invention, the cross formed by the at least two elongate elements may have an angle between two of the elongate elements in the range of 10° to 40°, e.g. in the range of 15° to 35°, e.g. in the range of 20° to 30°. It shall be clear to the skilled person that embodiments of the present invention may relate to any range formed by a lower limit selected from 10°, 15°, 20°, 30° and 35° and an upper limit (greater than the selected lower limit) selected from 15°, 20°, 30°, 35° and 40°.

In embodiments of the present invention, the cross may have an acute angle between two parts of respectively two elongate elements, in which these parts extend from the center of the cross to the frontal side.

In embodiments of the present invention, the cross may have an obtuse angle between two parts of respectively two elongate elements, in which these parts extend from the center of the cross to the frontal side.

It is an advantage of embodiments of the present invention that, by crossing multiple elongate elements, a small cross section of the motion constraining element can be provided near an axis of rotation of the human joint, such as to allow good bending of the motion constraining device near the axis of rotation, e.g. to prevent a restricted flexion due to folding of the material near the axis of rotation when the joint is flexed. It is a further advantage that regions where the motion constraining device engages the flexible sheath, e.g. corresponding to attachment points of the elongate elements, can be spaced apart around the circumference of the human member to enable a good protection against lateral and/or rotational deviations.

In embodiments according to the present invention, a first elongate element of the two elongate elements may extend from a position on the frontal side of the flexible sheath corresponding to a position of the shaft of the first phalanx to a position on the dorsal side of the flexible sheath corresponding to a position of the shaft of the second phalanx, and a second elongate element of the two elongate elements may extend from a position on the dorsal side of the flexible sheath corresponding to the position of the shaft of the first phalanx to a position on the frontal side of the flexible sheath corresponding to the position of the shaft of the second phalanx, when the flexible sheath is worn on the human finger.

It is an advantage of embodiments of the present invention that by forming a cruciate pulley system lateral to a human joint, a good protection against collateral damage due to lateral and/or rotational deviation can be provided.

In embodiments according to the present invention, a third elongate element may extend from a position on the lateral side of the flexible sheath corresponding to the position of the shaft of the first phalanx to a position on that lateral side of the flexible sheath corresponding to the position of the shaft of the second phalanx.

In embodiments according to the present invention, the first, second and/or third elongate element may comprise a thread, a wire, a yarn, a strip or a band composed of a stretch resistant material.

In embodiments according to the present invention, the first, second and/or third elongate element may be interwoven with or stitched into the flexible sheath.

In embodiments of the present invention, the flexible sheath may comprise at least one opening for exposing a dorsal aspect of the proximal and/or distal interphalangeal joint, e.g. a knuckle, when the flexible sheath is worn on the human finger. For example, the flexible sheath may have at least one opening for exposing a dorsal aspect of the joint, when the flexible sheath is worn on the human finger.

It is an advantage of embodiments of the present invention that a substantially unimpeded flexion and a good range of motion of the joint can be enabled.

In embodiments according to the present invention, the protective device may be an orthopaedic brace.

It is an advantage of embodiments of the present invention that motion of a joint can be allowed in a good range of motion when recovering from a collateral ligament injury, while protecting the joint from further harmful lateral and/or rotational deviations.

It is an advantage of embodiments of the present invention that a protection against collateral ligament injuries of the human finger due to lateral and/or rotational deviations is provided without substantially impeding or restricting the natural range of motion of the finger.

In embodiments according to the present invention, the or each motion constraining element may be secured to the flexible sheath in a first region corresponding to a position of the shaft of the first phalanx and the or each motion constraining element may also be secured to the flexible sheath in a second region corresponding to a position of the shaft of the second phalanx, when the flexible sheath is worn around the human finger.

In embodiments according to the present invention, the flexible sheath may comprise at least two annular elastic structures for exerting a compressive force on the human finger around the shaft of respectively the first phalanx and the second phalanx, when worn around the human finger, and the or each motion constraining element may be secured to the at least two annular elastic structures, e.g. the first end and the second end may be secured to corresponding annular elastic structures of the at least two annular structures.

It is an advantage of embodiments of the present invention that a compressive force can be exerted on the central part of the phalanges to support the internal anatomical structure of the finger. It is an advantage of embodiments of the present invention that annular elastic structures can be provided over the central part of the phalanges to improve grip. It is an advantage of embodiments of the present invention that annular elastic structures are provided to securely hold a motion constraining element in an aligned position with respect to a human finger. It is a further advantage of providing the annular elastic structures around the shaft of the phalanges, in accordance with embodiments of the present invention, that longitudinal displacement, along the medial axis of the finger, of the annular structures and/or of the motion constraining element secured by the annular structures is prevented, e.g. due to a narrow cross section of the finger at the shaft of the phalanges.

In embodiments according to the present invention, the or each motion constraining element may comprise at least two elongate elements fastened to or integrated in the flexible sheath, wherein the at least two elongate elements intersect to form a cross where an axis of rotation of the interphalangeal joint intersects the flexible sheath, when worn on the human finger.

It is an advantage of embodiments of the present invention that, by crossing multiple elongate elements, a small cross section of the motion constraining device can be provided near an axis of rotation of an interphalangeal joint, such as to allow good bending of the motion constraining device near the axis of rotation, e.g. to prevent a restricted flexion due to folding of the material near the axis of rotation when the digit is flexed. It is a further advantage that regions where the motion constraining device engages the flexible sheath, e.g. corresponding to attachment points of the elongate elements, can be spaced apart around the circumference of the finger to enable a good protection against lateral and/or rotational deviations.

In embodiments according to the present invention, a first elongate element of the two elongate elements may extend from a position on the palmar side of the flexible sheath corresponding to a position of the shaft of the first phalanx to a position on the dorsal side of the flexible sheath corresponding to a position of the shaft of the second phalanx, and a second elongate element of the two elongate elements may extend from a position on the dorsal side of the flexible sheath corresponding to said position of the shaft of the first phalanx to a position on the palmar side of the flexible sheath corresponding to the position of the shaft of the second phalanx, when the flexible sheath is worn on the human finger.

It is an advantage of embodiments of the present invention that by forming a cruciate pulley system lateral to a finger joint, a good protection against collateral damage due to lateral deviation can be provided, e.g. for lateral deviations ranging from a dorsal-lateral direction to a palmar-lateral direction.

In embodiments according to the present invention, the device may comprise a third elongate element extending from a position on the lateral side of the flexible sheath corresponding to the position of the shaft of the first phalanx to a position on the lateral side of the flexible sheath corresponding to the position of the shaft of the second phalanx.

In embodiments according to the present invention, the flexible sheath may comprise an opening for exposing a fingertip of the human finger when the flexible sheath is worn on the human finger, e.g. the flexible sheath may have an opening for exposing a fingertip of the human finger when the flexible sheath is worn on the human finger.

It is an advantage of embodiments of the present invention that good tactile sense and good grip can be enabled when the protective device is covering a finger, e.g. enclosing a finger while leaving a fingertip uncovered.

In embodiments of the present invention, the flexible sheath may comprise at least one opening for exposing a dorsal aspect of the interphalangeal joint of the human finger, when the flexible sheath is worn on the human finger. For example, the flexible sheath may have at least one opening for exposing a dorsal aspect of the interphalangeal joint of the human finger, when the flexible sheath is worn on the human finger.

It is an advantage of embodiments of the present invention that a substantially unimpeded flexion and a good range of motion of the finger can be enabled.

In embodiments of the present invention, the protective device may be a glove for wearing on a human hand, e.g. a sports glove, such as a glove for use in martial arts or combat sports or for use in climbing. The glove may comprise a plurality of flexible sheaths for wearing around a plurality of corresponding human fingers of the human hand, at least one of the at least four motion constraining elements being integrated in each of the flexible sheaths or secured to each of the flexible sheaths, in which bases of the flexible sheaths are joined together such as to form a connective textile covering at least a proximal part of a proximal phalanx of said human hand when the glove is worn. Particularly, the glove may comprise a plurality of protective devices in accordance with embodiments of the present invention as described hereinabove, e.g. four such protective devices for respectively four corresponding fingers.

It is an advantage of embodiments of the present invention that a plurality of fingers on a single hand can be easily protected against collateral ligament injury.

In embodiments according to the present invention, the glove may further comprise a wristband for enclosing a wrist of the human hand, and the connective textile may furthermore extend along an ulnar side of the human hand to connect to the wristband at the ulnar side, when the glove is worn.

In embodiments according to the present invention, the connective textile may extend along a radial side of the human hand, around a base of the thumb of the human hand, to connect to the wristband at the radial side, when the glove is worn.

In embodiments according to the present invention, the glove may further comprise a strap connecting the radial side of the connective textile to the ulnar side of the connective textile over a dorsal side of the human hand, such as to leave an opening between the strap and the bases of the flexible sheaths to expose dorsal aspects of the metacarpophalangeal joints of the human hand, when the glove is worn.

It is an advantage of embodiments of the present invention that a glove being worn may be held securely in place while leaving the hand palm and/or the metacarpophalangeal joints uncovered to allow a broad range of substantially unimpeded motion of the hand.

In embodiments according to the present invention, one of the plurality of flexible sheaths may be adapted for wearing around a thumb of the human hand, another of the plurality of flexible sheaths may be adapted for wearing around a forefinger of the human hand, and the connective textile may comprise a gusset connecting the flexible sheath for wearing around the thumb to the flexible sheath for wearing around the forefinger such that this gusset is stretched to a taut condition when the thumb is fully extended, when the glove is worn.

It is an advantage of embodiments of the present invention that protection can be provided against injury due to overextension of the thumb.

In embodiments according to the present invention, the flexible sheath and/or the connective textile may comprise a knitted, braided, woven and/or non-woven stretchable textile, such as for example a stretchable textile comprising neoprene, elastane, rubber, polyester, vinyl, velvet, vinyl and/or cotton.

In a second aspect, the present invention relates to a protective device for protecting a human joint for articulating a first bone with respect to a second bone, e.g. a human hinge joint, such as an elbow, a knee, an ankle or a digit joint. The protective device comprises a flexible sheath adapted for wearing around the human joint. The protective device also comprises at least one motion constraining element integrated in or secured to the flexible sheath. The or each of the at least one motion constraining element is adapted for constraining, when the flexible sheath is worn around the human joint, a lateral and/or rotational deviation motion of the first bone with respect to the second bone. The or each at least one motion constraining element covers a lateral side of the flexible sheath at a location corresponding to the human joint, when the flexible sheath is worn around the human joint. The or each at least one motion constraining element is adapted for resisting elongation of the motion constraining element in a longitudinal direction of the flexible sheath. The or each at least one motion constraining element is bendable in a direction to allow flexion of the human joint. The flexible sheath comprises at least two annular elastic structures for exerting a compressive force on the human body around the shaft of respectively the first bone and the second bone, when worn around the human joint, and the motion constraining element is secured to the at least two annular elastic structures.

It is an advantage of embodiments of the present invention that a compressive force can be exerted on the central part of the bones to support the internal anatomical structure. It is an advantage of embodiments of the present invention that annular elastic structures can be provided over the central part of the bones to improve grip. It is an advantage of embodiments of the present invention that annular elastic structures may be provided to securely hold a motion constraining element in an aligned position with respect to a human joint. It is a further advantage of providing the annular elastic structures around the shaft of the bones, in accordance with embodiments of the present invention, that longitudinal displacement of the annular structures and/or of the motion constraining element secured by the annular structures is prevented, e.g. due to a narrow cross section of the human member at the shaft of the bones.

In a third aspect, the present invention relates to a protective device for protecting a human joint for articulating a first bone with respect to a second bone, e.g. a human hinge joint, such as an elbow, a knee, an ankle or a digit joint. The protective device comprises a flexible sheath adapted for wearing around the human joint. The protective device also comprises at least one motion constraining element integrated in or secured to the flexible sheath. The or each of the at least one motion constraining element is adapted for constraining, when the flexible sheath is worn around the human joint, a lateral and/or rotational deviation motion of the first bone with respect to the second bone. The or each at least one motion constraining element covers a lateral side of the flexible sheath at a location corresponding to the human joint, when the flexible sheath is worn around the human joint. The or each at least one motion constraining element is adapted for resisting elongation of the motion constraining element in a longitudinal direction of the flexible sheath. The or each at least one motion constraining element is bendable in a direction to allow flexion of the human joint. The or each motion constraining element comprises at least three elongate elements fastened to or integrated in the flexible sheath, wherein the at least three elongate elements intersect to form a cross where an axis of rotation of the human joint intersects the flexible sheath, when worn on the human joint, e.g. to form a cross at a point where an imaginary axis, perpendicular to the plane of motion in which the articulation motion of the joint occurs, projects through the pivot point of the joint. A first elongate element of the at least three elongate elements extends from a position on the frontal side of the flexible sheath corresponding to a position of the shaft of the first bone to a position on the dorsal side of the flexible sheath corresponding to a position of the shaft of the second bone, and a second elongate element of the at least three elongate elements extends from a position on the dorsal side of the flexible sheath corresponding to the position of the shaft of the first bone to a position on the frontal side of the flexible sheath corresponding to the position of the shaft of the second bone, when the flexible sheath is worn on the human joint. A third elongate element (of the at least three elongate elements) extends from a position on the lateral side of the flexible sheath corresponding to the position of the shaft of the first bone to a position on that lateral side of the flexible sheath corresponding to the position of the shaft of the second bone.

It is an advantage of embodiments of the present invention that, by crossing multiple elongate elements, a small cross section of the motion constraining element can be provided near an axis of rotation of the human joint, such as to allow good bending of the motion constraining device near the axis of rotation, e.g. to prevent a restricted flexion due to folding of the material near the axis of rotation when the joint is flexed. It is a further advantage that regions where the motion constraining device engages the flexible sheath, e.g. corresponding to attachment points of the elongate elements, can be spaced apart around the circumference of the human member to enable a good protection against lateral and/or rotational deviations.

It is an advantage of embodiments of the present invention that by forming a cruciate pulley system lateral to a human joint, a good protection against collateral damage due to lateral and/or rotational deviation can be provided.

The flexible sheath may comprise at least two annular elastic structures for exerting a compressive force on the human body around the shaft of respectively the first bone and the second bone, when worn around the human joint, and the motion constraining element is secured to the at least two annular elastic structures.

In embodiments of the first, second and/or third aspect of the present invention, the flexible sheath may be structure for enveloping the joint, e.g. at least part of a human member comprising the joint, in a close-fitting manner. The sheath may be a tubular structure. Particularly, the sheath may enclose at least part of a human member comprising the joint around the entire cross-sectional circumference of the member on both sides of the joint, e.g. may enclose the member around the first bone around its entire circumference and may enclose the member around the second bone around its entire circumference, both enclosing parts for enclosing respectively the first bone and the second bone being connected. However, the sheath is not necessarily continuous over its entire surface area, e.g. may comprise holes, insofar a continuous and closed path is formed around the entire member, e.g. such as to exert a compressive force on the member, on both sides of the joint. For example, the flexible sheath may comprise or even consist of at least two annular elastic structures for exerting a compressive force on the human body around the shaft of respectively the first bone and the second bone, when worn around the human joint, and the motion constraining element may be secured to the at least two annular elastic structures, thus forming a connection between the enclosing parts for enclosing respectively the first bone and the second bone. However, preferably, the sheath may also comprise a flexible textile connecting such annular elastic structures to aid in applying the protective device on the body, aligning the protective device to the anatomical features of the body when worn and to increase comfort when worn.

In embodiments of the first, second and/or third aspect of the present invention, the protective device may comprise two of the motion constraining elements respectively covering each lateral side of the flexible sheath at opposite lateral locations of the human joint, when the flexible sheath is worn around the human joint.

In embodiments of the first, second and/or third aspect of the present invention, the first, second and/or third elongate element may comprise a thread, a wire, a yarn, a strip or a band composed of a stretch resistant material.

In embodiments of the first, second and/or third aspect of the present invention, the first, second and/or third elongate element may be interwoven with or stitched into the flexible sheath.

In embodiments of the first, second and/or third aspect of the present invention, the flexible sheath may comprise at least one opening for exposing a dorsal aspect of the human joint, e.g. a knuckle, or a frontal aspect of the human joint, e.g. a patella, when the flexible sheath is worn on the human joint. For example, the flexible sheath may have at least one opening for exposing a dorsal aspect of the human joint, or a frontal aspect of the human joint, when the flexible sheath is worn on the human joint.

It is an advantage of embodiments of the present invention that a substantially unimpeded flexion and a good range of motion of the joint can be enabled.

In embodiments of the first, second and/or third aspect of the present invention, the protective device may be an orthopaedic brace.

It is an advantage of embodiments of the present invention that motion of a joint can be allowed in a good range of motion when recovering from a collateral ligament injury, while protecting the joint from further harmful lateral and/or rotational deviations.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
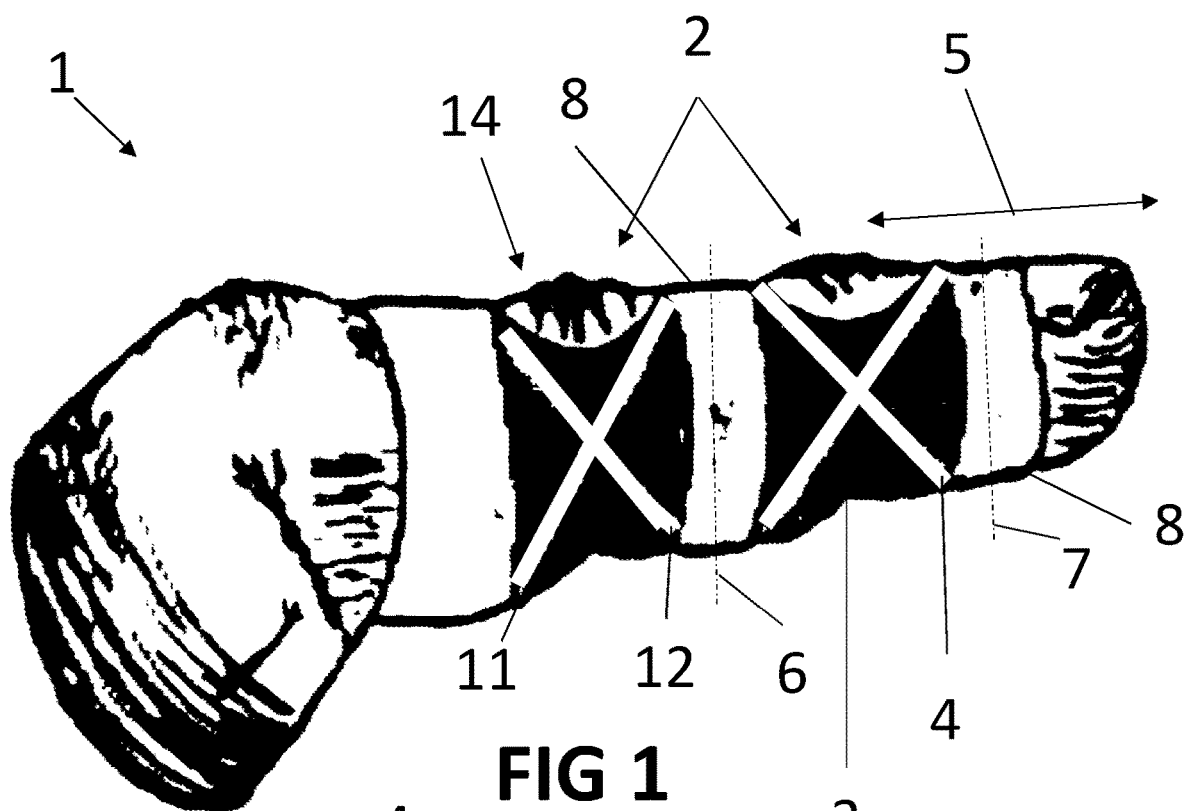
FIG. 1 shows a first exemplary embodiment of a protective device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first, second and third aspect, the present invention relates to a protective device for protecting a human joint, e.g. a human joint for articulating a first bone with respect to, e.g. relative to, a second bone.

The protective device comprises a flexible sheath adapted for wearing around the human joint, and at least one motion constraining element integrated in or secured to the flexible sheath.

Each motion constraining element is adapted for constraining, when the flexible sheath is worn around the human joint, e.g. around the human finger, a lateral and/or rotational deviation motion of the first bone, e.g. a first phalanx, with respect to the second bone, e.g. a second phalanx. Each motion constraining element covers a lateral side of the flexible sheath at a location corresponding to the joint, when the flexible sheath is worn around the human joint, e.g. around the finger. Each motion constraining element is adapted for resisting elongation of the motion constraining element in a longitudinal direction of the flexible sheath. Each motion constraining element is bendable in a direction to allow flexion of the human joint.

While embodiments of the first, second and third aspect of the present invention share the features described hereinabove, embodiments of the first, second and third aspect differ with respect to each other in the additional features as described hereinbelow. Embodiments of the present invention may also relate to a combination of the features of the first aspect, the second aspect and/or the third aspect.

Particularly, the protective device in accordance with embodiments of the first aspect of the present invention is adapted for protecting a proximal interphalangeal joint and a distal interphalangeal joint of a human finger. Four of the motion constraining elements correspond to respectively each of both lateral sides of each of the proximal interphalangeal joint and the distal interphalangeal joint of the human finger. The motion constraining elements corresponding to the distal interphalangeal joint and the motion constraining elements corresponding to the proximal interphalangeal joint are distinct and separate elements having different points of engagement on the flexible sheath.

While the reference to a point of engagement may refer to a clearly distinct point where the motion constraining element is joined to the flexible sheath, e.g. where it is affixed thereto, this is not necessarily the case for each embodiment in accordance with the present invention. For example, the motion constraining element may be integrally formed with the flexible sheath, e.g. by a continuous or discontinuous change of material properties or composition of the flexible sheath. Nevertheless, the point of engagement may still be identified with a point or discrete region where the properties of the flexible sheath changes into the properties of the motion constraining element, e.g. where a flexible material changes into a more rigid material. For example, embodiments not necessarily limited thereto, the flexible sheath and the motion constraining elements may be integrally formed by knitting, braiding, weaving or otherwise composing a textile from a yarn, fiber or other elongate component structure, in which the material properties of such elongate component structure may be locally altered, e.g. by adding a resin or thermoplastic material, such as a coating of the yarn or fiber, to obtain suitable properties of the textile at that location for implementing the motion constraining element.

The protective device in accordance with embodiments of the second aspect of the present invention, which is not necessarily limited to a protective device for a human finger, comprises at least two annular elastic structures for exerting a compressive force on the human body around the shaft of respectively the first bone and the second bone, when worn around the human joint, and the motion constraining element is secured to the at least two annular elastic structures.

In the protective device in accordance with embodiments of the third aspect of the present invention, which is not necessarily limited to a protective device for a human finger and/or a protective device comprising at least two annular elastic structures, the or each motion constraining element comprises at least three elongate elements fastened to or integrated in the flexible sheath, wherein the at least three elongate elements intersect to form a cross (i.e. intersect all three in substantially a single common center) where an axis of rotation of the human joint intersects the flexible sheath, when worn on the human joint, e.g. to form a cross at a point where an imaginary axis, perpendicular to the plane of motion in which the articulation motion of the joint occurs, projects through the pivot point of the joint. A first elongate element of the at least three elongate elements extends from a position on the frontal side of the flexible sheath corresponding to a position of the shaft of the first bone to a position on the dorsal side of the flexible sheath corresponding to a position of the shaft of the second bone, and a second elongate element of the at least three elongate elements extends from a position on the dorsal side of the flexible sheath corresponding to the position of the shaft of the first bone to a position on the frontal side of the flexible sheath corresponding to the position of the shaft of the second bone, when the flexible sheath is worn on the human joint. A third elongate element (of the at least three elongate elements) extends from a position on the lateral side of the flexible sheath corresponding to the position of the shaft of the first bone to a position on that lateral side of the flexible sheath corresponding to the position of the shaft of the second bone.

In the description hereinbelow, features, e.g. essential and/or optional features, of embodiments of the present invention are further described in detail. It shall be understood that the described features may equally relate to embodiments of the first, the second and the third aspect of the present invention, e.g. due to the similarities between the different aspects of the present invention, unless a combination of a feature as described is clearly contradictory to or incompatible with the distinctive features of a particular aspect as described hereinabove.

Figure 2:
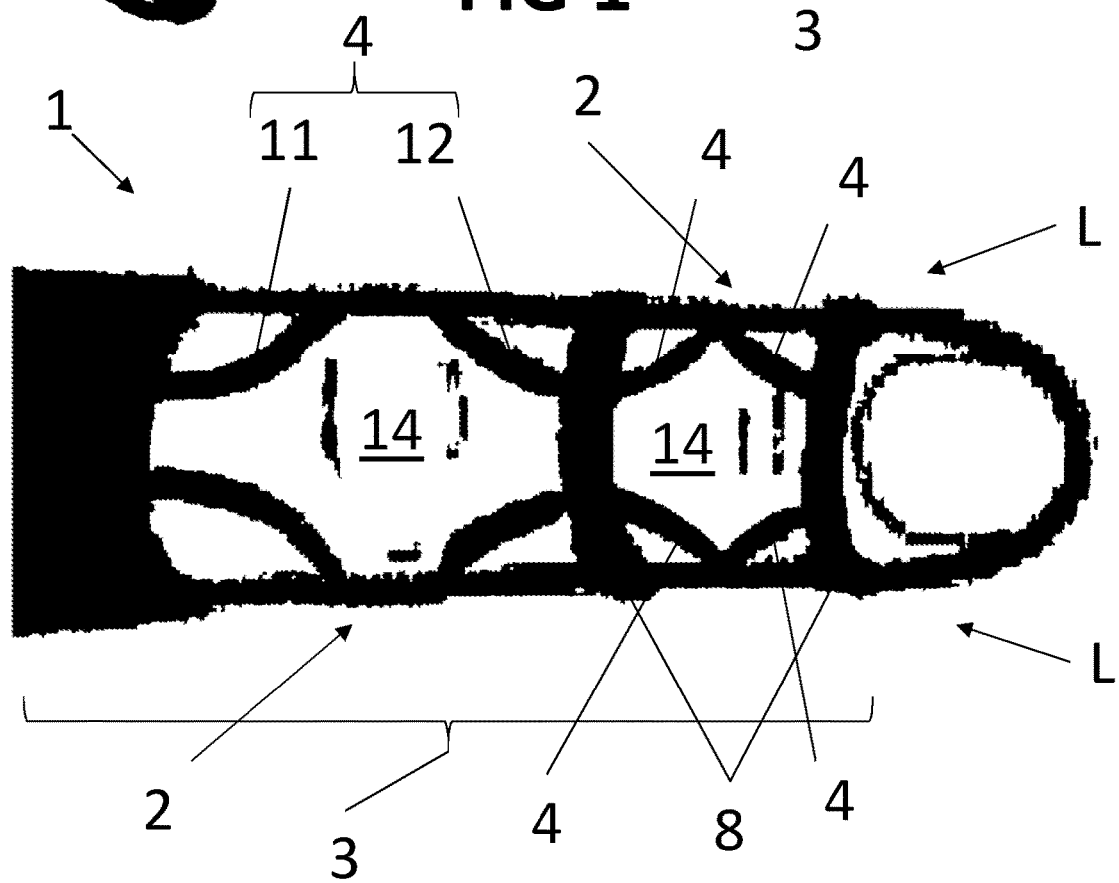
FIG. 2 shows a first exemplary embodiment of a protective device in accordance with embodiments of the present invention.

Referring to FIG. 1 and FIG. 2, an exemplary embodiment of a protective device 1 in accordance with embodiments of the present invention is shown. The protective device 1 may for example be an orthopaedic brace.

FIG. 1 and FIG. 2 show a protective device 1 for protecting a human joint 2, e.g. joints 2 of a human finger. As illustrated in FIG. 1 and FIG. 2, the protective device may be adapted for protecting a plurality of human joints 2, e.g. multiple joints of a finger. The protective device 1 may be adapted for protecting a human finger.

However, embodiments of the present invention are not limited thereto, and may equally relate to other joints of the human body for articulating a first bone with respect to a second bone, e.g. protecting a hinge joint of the human body, such as an elbow, a knee, a toe joint or an ankle.

The protective device 1 comprises a flexible sheath 3 adapted for wearing around the human joint 2.

For example, the flexible sheath 3 may be adapted for wearing around an interphalangeal joint that connects a first phalanx of the human finger to a second phalanx of the human finger, the second phalanx being adjacent to the first phalanx. The flexible sheath 3 may be adapted for wearing around two interphalangeal joints of the human finger. Thus, the flexible sheath 3 may comprise a palmar side for covering a palmar face of the human finger, a dorsal side for covering a dorsal face of the human finger and two lateral sides for covering respectively an ulnar and a radial face of the human finger. The palmar side, the dorsal side and the two lateral sides may refer to surface aspects of the flexible sheath, and do not necessarily imply a clear structural separation and/or delineation of these sides. For example, the flexible sheath may have a substantially tubular shape, and quadrants around the circumference of the tubular structure for covering corresponding aspects of the finger when worn may be referred to as the respective sides.

The flexible sheath and/or the connective textile may comprise a knitted, braided, woven and/or non-woven stretchable textile.

The flexible sheath 3 may have at least one opening 14 for exposing a dorsal aspect of the human joint, when the flexible sheath is worn on the human joint.

Furthermore, the flexible sheath 3 of a protective device 1 for protecting a finger in accordance with embodiments of the present invention may have an opening for exposing a fingertip of the human finger when the flexible sheath 3 is worn on the human finger.

The protective device 1 further comprises at least one motion constraining element 4 integrated in or secured to the flexible sheath 3. For example, the at least one motion constraining element may be woven into, stitched to or glued onto the sheath, and/or may be fixed to the sheath at predetermined connection points, e.g. by staples, stitches, nail rivets, screws, buttons and/or similar fasteners.

While the motion constraining element may be a clearly distinct structure affixed to or joined to the flexible sheath, this is not necessarily the case for each embodiment in accordance with the present invention. For example, the motion constraining element may be integrally formed with the flexible sheath, e.g. by a continuous or discontinuous change of material properties or composition of the flexible sheath. Nevertheless, a change of the properties of the flexible sheath into the properties of the motion constraining element would still allow an unambiguous identification of the features represented by the flexible sheath and the motion constraining element. For example, a flexible material may change into a more rigid material where the motion constraining element is implemented. For example, embodiments not necessarily limited thereto, the flexible sheath and the motion constraining elements may be integrally formed by knitting, braiding, weaving or otherwise composing a textile from a yarn, fiber or other elongate component structure, in which the material properties of such elongate component structure may be locally altered, e.g. by adding a resin or thermoplastic material, such as a coating of the yarn or fiber, to obtain suitable properties of the textile at that location for implementing the motion constraining element.

The at least one motion constraining element 4 is adapted for constraining, when the flexible sheath 3 is worn around the human joint 2, a lateral and/or rotational deviation motion of the first bone with respect to the second bone. For example, the at least one motion constraining element 4 may be adapted for constraining, when the flexible sheath 3 is worn around the human finger, a lateral and/or rotational deviation motion of the first phalanx with respect to the second phalanx, in which the first and the second phalanx are connected by the interphalangeal joint.

The at least one motion constraining element 4 covers a lateral side L of the flexible sheath 3 at a location corresponding to the human joint 2, when the flexible sheath is worn around the human joint. For example, each motion constraining element 4 may cover one of the lateral sides L of the flexible sheath at a location corresponding to the interphalangeal joint, when the flexible sheath is worn around the human finger.

The at least one motion constraining element 4 is adapted for resisting elongation of the motion constraining element 4 in a longitudinal direction 5 of the flexible sheath 3.

The at least one motion constraining element 4 is bendable in a direction to allow flexion of the human joint 2.

For example, the at least one motion constraining element 4, in a protective device for protecting an interphalangeal joint of a human finger in accordance with embodiments of the present invention, may be bendable in a dorso-palmar direction to allow flexion of the interphalangeal joint, when the flexible sheath is worn around the human finger.

The protective device 1 may comprise two of the motion constraining elements 4 respectively covering each lateral side L of the flexible sheath at opposite lateral locations of the human joint 2, when the flexible sheath is worn around the human joint 2.

The protective device 1 may comprise four of the motion constraining elements 4 for respectively each of both lateral sides L of each of a proximal interphalangeal joint and a distal interphalangeal joint of a human finger. Thus, respectively four motion constraining elements 4 may be integrated in or secured to the flexible sheath 3, in which these four motion constraining elements respectively cover a first lateral side of the flexible sheath 3 at a location corresponding to a radial side of a proximal interphalangeal joint of a human finger, a second lateral side of the flexible sheath 3 at a location corresponding to an ulnar side of the proximal interphalangeal joint, the first lateral side of the flexible sheath 3 at a location corresponding to a radial side of a distal interphalangeal joint of the human finger and the second lateral side of the flexible sheath 3 at a location corresponding to an ulnar side of the distal interphalangeal joint.

In embodiments of the first aspect of the present invention, the motion constraining elements corresponding to the distal interphalangeal joint and the motion constraining elements corresponding to the proximal interphalangeal joint are distinct and separate elements having different points of engagement on the flexible sheath.

It is an advantage of embodiments that, by providing for each interphalangeal joint separate motion constraining elements that engage with the flexible sheath in different points, the motion constraints imposed on each joint can be independently controlled. The motion constraining element 4 may be secured to the flexible sheath 3 in a first region 6 corresponding to a position of the shaft of the first bone and the motion constraining element 4 may be secured to the flexible sheath in a second region 7 corresponding to a position of the shaft of the second bone, when the flexible sheath 3 is worn around the human joint.

The flexible sheath 3 may comprise at least two annular elastic structures 8 for exerting a compressive force on the human body around the shaft of respectively the first bone and the second bone, when the flexible sheath is worn around the human joint, e.g. around respectively the first region 6 and the second region 7. The motion constraining element 4 may be secured to the at least two annular elastic structures, e.g. to the first annular elastic structure at a first end of the motion constraining element 4 in the first region 6 and to the second annular elastic structure at a second end of the motion constraining element 4 in the second region 7.

However, the flexible sheath may also be an integrally formed compressive structure, e.g. a compression glove. For example, the flexible sheath may be adapted for being more compressive, when worn, around the middle of the (or each) phalanx. Thus, a same effect as provided by annular elastic structures may be achieved by an integrally formed flexible sheath without clearly distinct annular structures.

Such compressive glove structures are known in the art. For example, for the management of oedema and/or arthritis. While embodiments of the present invention may comprise such compressive structure as known in the art, such compression glove is not necessarily identically configured. For example, for the uses known in the prior art, e.g. in medical applications such as the oedema and/or arthritis care, a different, e.g. higher, compressive force may be required than for the use in accordance with embodiments of the present invention. In accordance with embodiments of the present invention, a compressive force may be exerted on the finger and/or hand such as to ensure that sufficient friction can be generated between the glove structure and the body, i.e. such that the motion constraining elements remain substantially stationary, e.g. well-aligned, with respect to the finger and can generate a sufficient constraining force between ends thereof on opposite sides of the joint to protect the joint. Optimization of a known compression glove structure, e.g. optimization of design parameters thereof, to achieve a sufficient yet comfortable compressive force on the finger is considered an activity that lies well within the capabilities of the skilled person without requiring the exertion of an inventive effort.

The motion constraining element 4, e.g. each motion constraining element 4, may comprise at least two elongate elements 11,12 fastened to or integrated in the flexible sheath 3. The at least two elongate elements may intersect to form a cross where an axis of rotation of the human joint intersects the flexible sheath, when worn on the human joint, as shown in FIG. 1.

Where reference is made to a 'cross', this is not necessarily limited to two crossing elements, but this may also refer to any number of elements, such as three, intersecting in substantially a same point.

In embodiments of the present invention, the cross formed by the at least two elongate elements may have an angle between two of the elongate elements in the range of 10° to 40°, e.g. in the range of 15° to 35°, e.g. in the range of 20° to 30°. Other ranges between any pair of the mentioned endpoints are also contemplated.

In embodiments of the present invention, the cross may have an acute angle between two parts of respectively two elongate elements, in which these parts extend from the center of the cross to the frontal side. In embodiments of the present invention, the cross may have an obtuse angle between two parts of respectively two elongate elements, in which these parts extend from the center of the cross to the frontal side.

Figure 8:
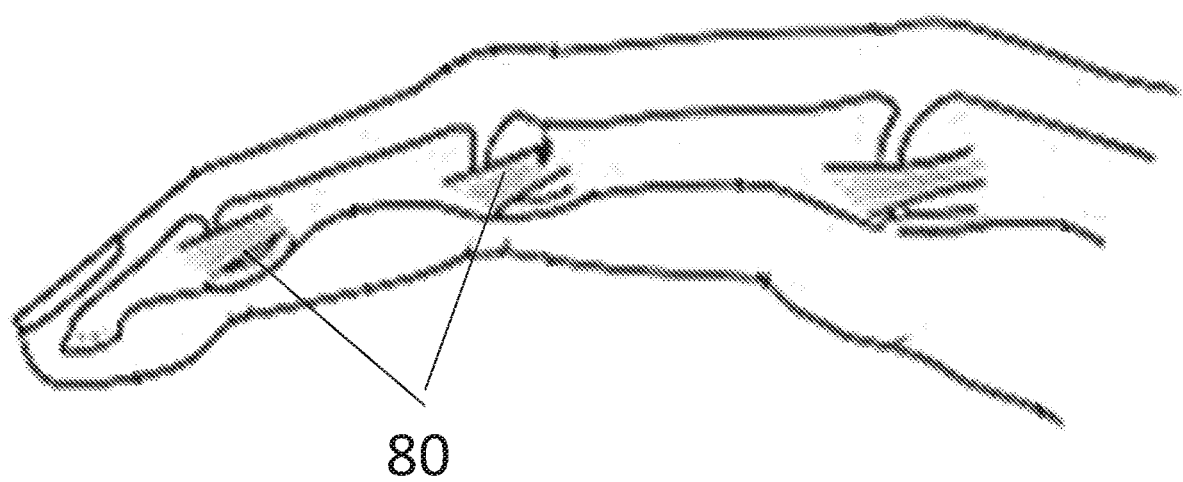
FIG. 8 shows an anatomical representation of a finger to illustrate aspects of embodiments of the present invention.

For example, referring to FIG. 8, the elongate elements may be configured such as to be parallel, or substantially parallel, with the collateral ligaments 80, when the flexible sheath is worn. Thus, the motion constraining elements may mimic the function of the collateral ligaments.

Alternatively, the elongate elements may be configured such as to be perpendicular, or substantially perpendicular, to the collateral ligaments 80, when the flexible sheath is worn. For example, the motion constraining elements may engage with the flexible sheath at a short distance to the knuckle, e.g. substantially away from the middle points of the shafts of the phalanges. Thus, a larger impact force can be absorbed by the elongate elements when pulled taut.

For example, when the elongate elements were to form a continuous band around the finger covering both the proximal and the distal interphalangeal joint, only a suboptimal protection might be achieved. One helix would connect the rotation point of a knuckle, over the phalanx, to the rotation point on the opposite lateral side of the next knuckle. Consider the radius at the first knuckle to be $R_1$ and the radius at the second knuckle to be $R_2$, where $R_2 < R_1$, while the length of the (middle) phalanx is L. The path of such hypothetical continuous band can be expressed as:

$$\begin{cases} x = \frac{h-z}{h} R_1 \cos\left(\frac{\pi}{L} z\right) \\ y = \frac{h-z}{h} R_1 \sin\left(\frac{\pi}{L} z\right) \\ z = z \end{cases}$$

$$\text{with } h = \frac{R_1 L}{R_1 - R_2}$$

and z a coordinate along the longitudinal axis of the finger, y a coordinate in the dorso-palmar direction.

Using this model, the angle that the helix makes with the vertical direction y can be estimated. For example, for typical values of $R_1 = 5.7/2\pi$, $R_2 = 5/2\pi$, $L = 3$, then at the first knuckle (between proximal and middle phalanx), an angle of 46.5 degrees of obtained, while at the second knuckle (between middle and distal phalanx) an angle of 50.2 degrees is obtained. Thus, using such continuous band, the angles are fixed and dependent on the geometry of the finger, with angles in the range of about 45 degrees to about 50 degrees. However, such angles may not be optimal.

In accordance with embodiments of the present invention, an elongate element may be fixed in a connection point at a distance, measured in the longitudinal direction, from the rotation point in the range of 2 mm to 10 mm, e.g. in the range of 3 mm to 5 mm, e.g. 3 mm. For example, the connection point may be at a distance, measured in the dorso-palmar direction in the range of 3 mm to 8 mm, e.g. in the range of 4 mm to 6 mm, e.g. 5 mm.

For example, with a connection 3 mm to the left and right of the rotation point, but 5 mm above and below this point, an angle of 31 degrees can be obtained.

A first elongate element 11 of the at least two elongate elements may extend from a position on the frontal side of the flexible sheath corresponding to a position of the shaft of the first bone to a position on the dorsal side of the flexible sheath corresponding to a position of the shaft of the second bone, and a second elongate element 12 of the two elongate elements may extend from a position on the dorsal side of the flexible sheath corresponding to the position of the shaft of the first bone to a position on the frontal side of the flexible sheath corresponding to the position of the shaft of the second bone, when the flexible sheath is worn on the human joint.

Figure 3:
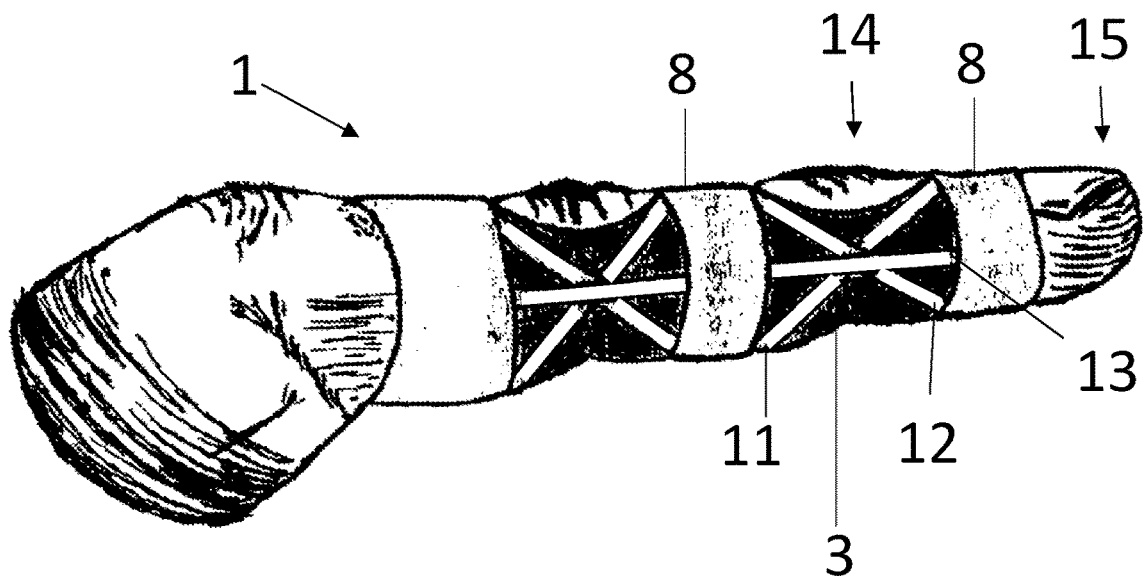
FIG. 3 shows a second exemplary embodiment of a protective device in accordance with embodiments of the present invention.
Figure 4:
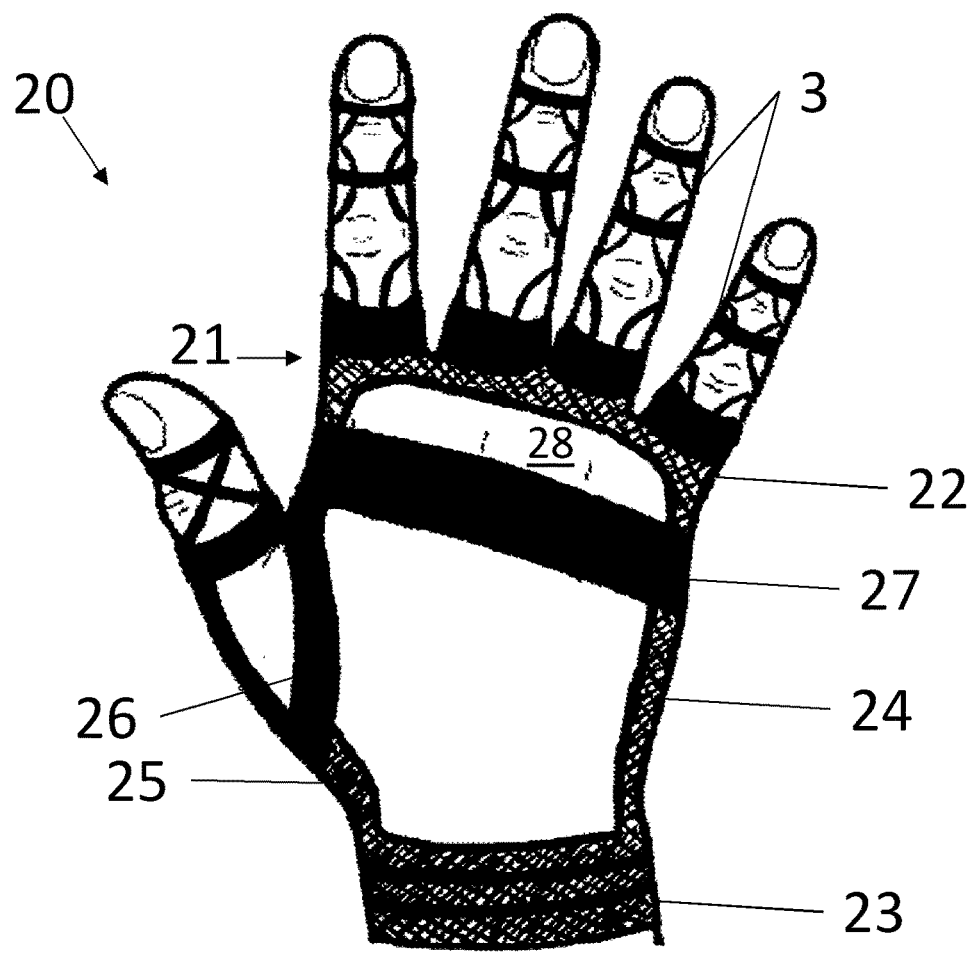
FIG. 4 shows a dorsal view of an exemplary embodiment of a protective glove in accordance with embodiments of the present invention.
Figure 5:
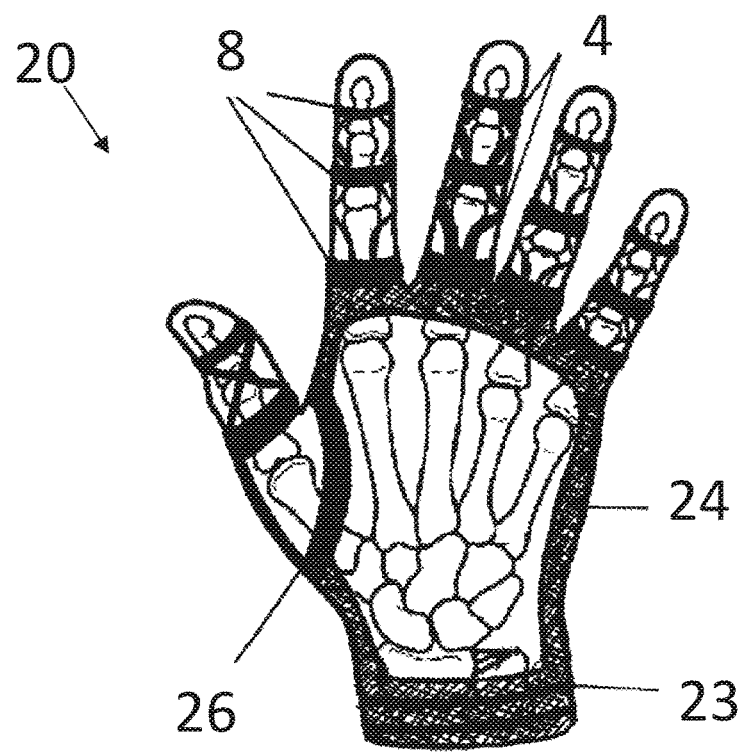
FIG. 5 shows a dorsal view, with an anatomical overlay of bone structures, of an exemplary embodiment of a protective glove in accordance with embodiments of the present invention.

As shown in FIG. 3, the device, e.g. the at least one motion constraining element 4, may further comprise a third elongate element 13 that extends from a position on the lateral side of the flexible sheath 3 corresponding to the position of the shaft of the first bone to a position on that lateral side of the flexible sheath corresponding to the position of the shaft of the second bone.

Referring again to FIG. 8, it can be seen that the third elongate element may approximate the roughly horizontal orientation of the collateral ligaments 80.

Furthermore, in embodiments of the present invention, the at least one motion constraining element may comprise a plurality of elongate elements, e.g. more than three, such as 5 or even more, e.g. 10 or even more, oriented in a plurality of different orientations, for example ranging from a horizontal alignment (e.g. parallel to the longitudinal axis) to 45° between the longitudinal and dorsopalmar direction, or even to 80° with respect to the longitudinal direction, e.g. almost vertical in the dorsopalmar direction. The plurality of elongate elements may be clearly distinct elongate elements, or may be co-integrated, e.g. as strands oriented in the different directions in a composite textile.

The elongate elements 11,12,13 may comprise a thread, a wire, a yarn, a strip and/or a band composed of a stretch resistant material.

The elongate elements 11,12,13 may be interwoven with or stitched into the flexible sheath.

Referring to FIG. 4 to FIG. 7, the protective device in accordance with embodiments of the present invention may be a glove 20 for wearing on a human hand. The glove 20 may comprise a plurality of flexible sheaths 3, e.g. as described hereinabove, for wearing around a plurality of corresponding human fingers of the human hand. At least one of the at least one motion constraining element 4 is integrated in each of the flexible sheaths 3, or secured to each of the flexible sheaths 3. Each of the flexible sheaths 3 may comprise at least one of the at least one motion constraining element 4.

Bases 21 of the flexible sheaths may be joined together such as to form a connective textile 22 covering at least a proximal part of a proximal phalanx of the human hand when the glove is worn.

The glove 20 may comprise a wristband 23 for enclosing a wrist of said human hand, in which the connective textile 22 extends along an ulnar side 24 of the human hand to connect to the wristband 23 at the ulnar side, when the glove is worn.

The connective textile may also extend along a radial side 25 of the human hand, around a base of the thumb of the human hand, to connect to the wristband 23 at the radial side, when the glove is worn. Furthermore, a thumb support 26 may be provided around the base of the thumb, e.g. to support the carpometacarpal joint, e.g. an elastic structure exerting a compressive force on the carpometacarpal joint when the glove 20 is worn.

The glove 20 may comprise a strap 27 connecting the radial side 25 of the connective textile 22 to the ulnar side 24 of the connective textile over a dorsal side of the human hand, when the glove is worn. An opening 28 may be formed between the strap 27 and the bases 21 of the flexible sheaths to expose dorsal aspects of the metacarpophalangeal joints of the human hand, when the glove is worn.

Figure 6:
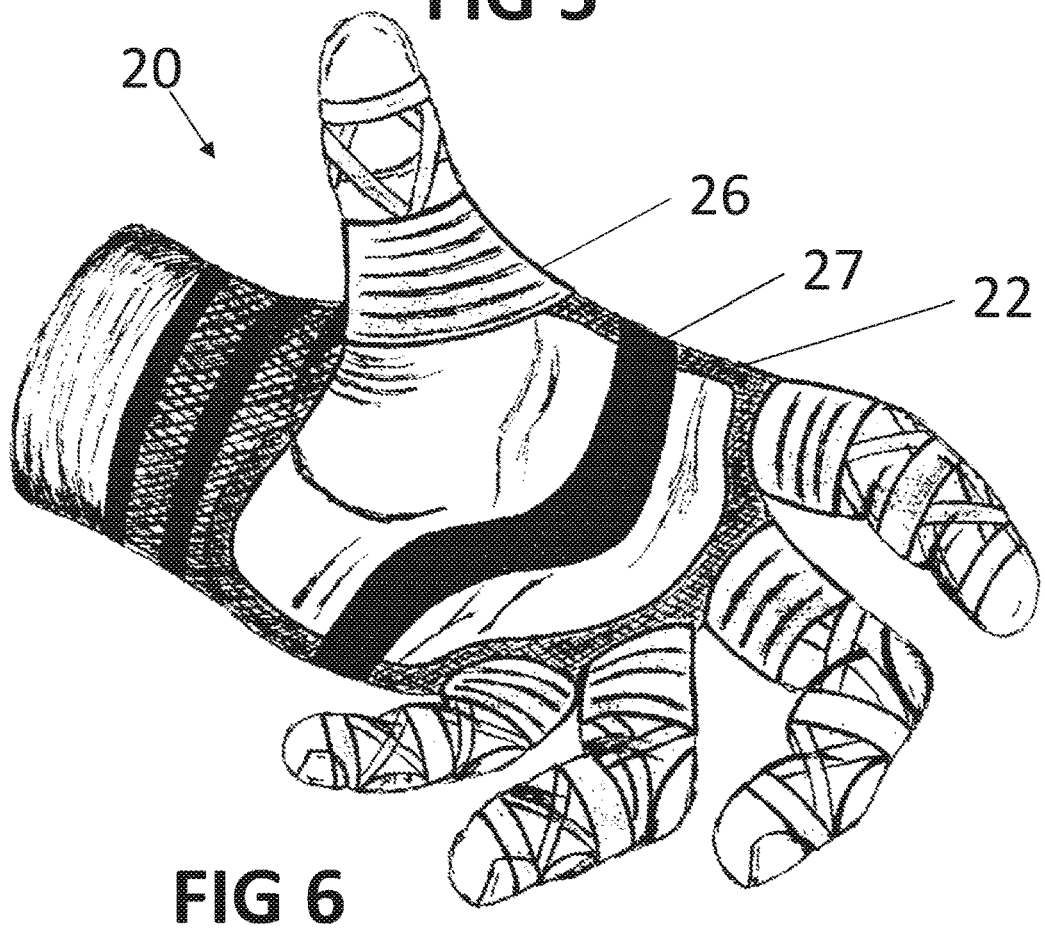
FIG. 6 shows a glove in accordance with embodiments of the present invention.
Figure 7:
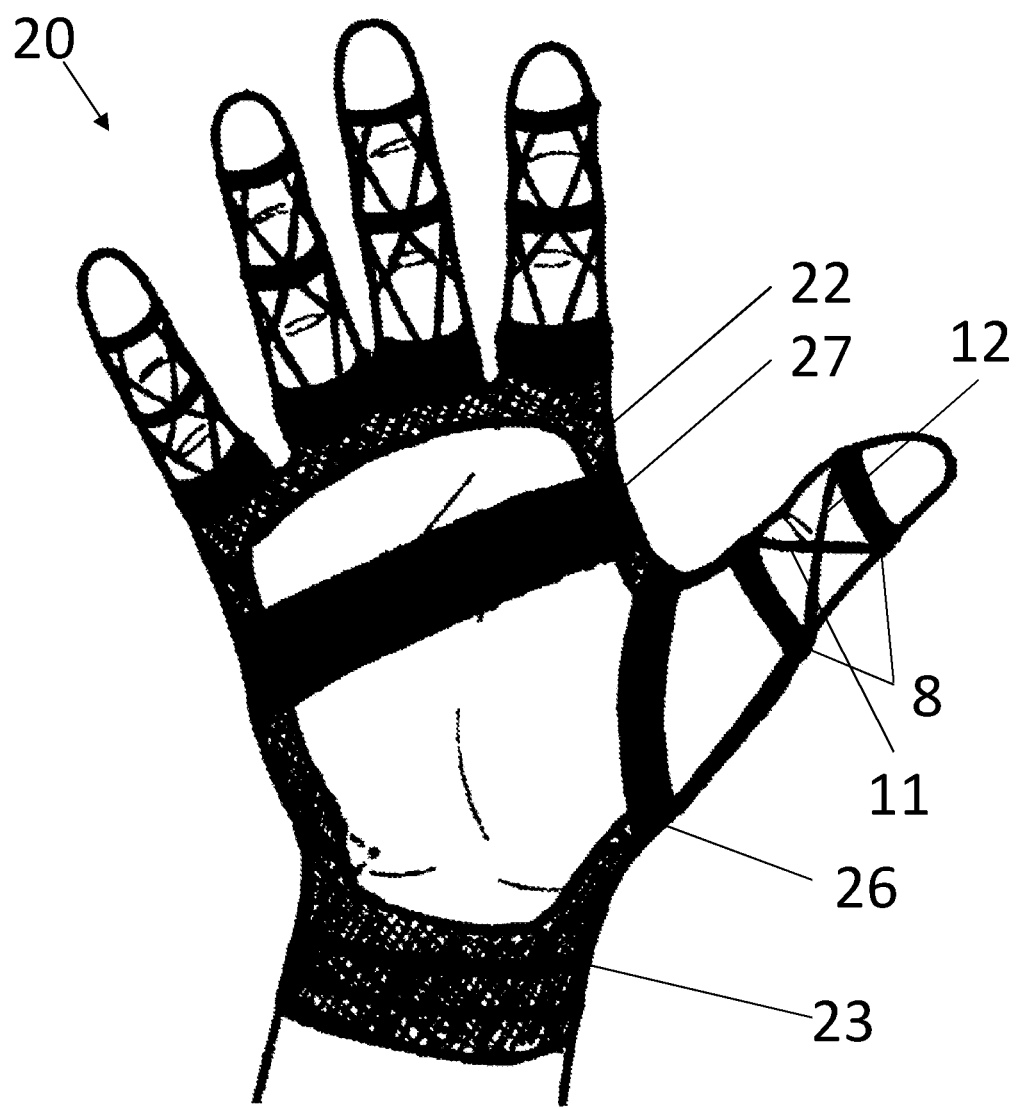
FIG. 7 shows a palmar view of a glove in accordance with an exemplary embodiment of the present invention.

Furthermore, the strap 27, or another strap, may also connect the radial side of the connective textile to the ulnar side of the connective textile over a palmar side of the human hand, when the glove is worn, e.g. as shown in FIG. 6.

One flexible sheath of the plurality of flexible sheaths may be adapted for wearing around a thumb of the human hand, another of the plurality of flexible sheaths may be adapted for wearing around a forefinger of the human hand.

Figure 9:
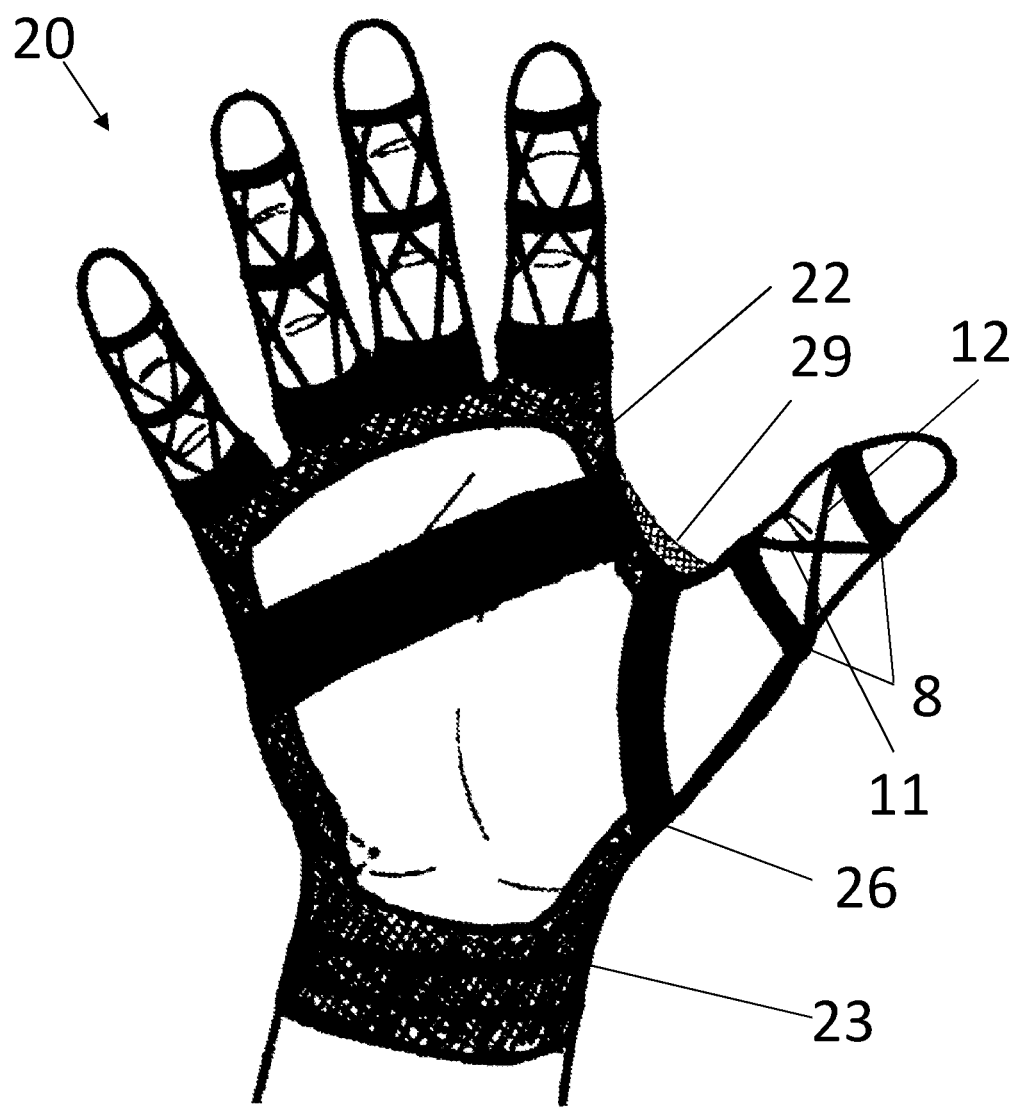
FIG. 9 shows a palmar view of a glove in accordance with another exemplary embodiment of the present invention.

Referring to FIG. 9, the connective textile may comprise a gusset 29 connecting the flexible sheath for wearing around the thumb to the flexible sheath for wearing around the forefinger such that the gusset 29 is stretched to a taut condition when the thumb is fully extended, when the glove is worn.

The connective textile 22 may comprise a braided, knitted, woven and/or non-woven stretchable textile.

The invention claimed is:

1. A protective device for protecting a proximal interphalangeal joint and a distal interphalangeal joint of a human finger when worn, said protective device comprising:

a flexible sheath adapted for wearing around said human finger, wherein said flexible sheath comprises a palmar side for covering a palmar face of said human finger when worn, a dorsal side for covering a dorsal face of said human finger when worn and two lateral sides for covering respectively an ulnar and a radial face of said human finger when worn, and at least two proximal motion constraining elements integrated in or secured to said flexible sheath at a proximal portion and at least two distal motion constraining elements, integrated in or secured to said flexible sheath at a distal portion of said flexible sheath, said proximal portion and said distal portion of the flexible sheath corresponding to respectively each of both lateral sides of said proximal interphalangeal joint of said human finger when said flexible sheath is worn and each of both lateral sides corresponding to said distal interphalangeal joint of said human finger when said flexible sheath is worn, wherein each of the at least two proximal motion constraining elements and each of the at least two distal motion constraining elements is adapted for constraining, when said flexible sheath is worn around said human finger, a lateral and/or rotational deviation motion of a first phalanx with respect to a second phalanx, said first and second phalanx being articulated with respect to each other by said interphalangeal joint to which said motion constraining element corresponds when worn, wherein each of the at least two proximal motion constraining elements covers a lateral side of the flexible sheath at the proximal portion and each of the at least two distal-motion constraining elements covers a lateral side of the flexible sheath at distal portion of said flexible sheath, said proximal portion corresponding to said proximal interphalangeal joint and said distal portion corresponding to said distal interphalangeal joint when the flexible sheath is worn around said human finger, wherein each of the at least two proximal motion constraining elements and each of the at least two distal motion constraining elements is adapted for resisting elongation in a longitudinal direction of the flexible sheath, wherein at least one motion constraining element of the at least two proximal motion constraining elements and of the at least two distal motion constraining elements is bendable in a dorso-palmar direction to allow flexion of the interphalangeal joint, when said flexible sheath is worn around said human finger, wherein the at least two distal motion constraining elements are distinct and separate elements from the at least two proximal motion constraining elements, having different points of engagement on the flexible sheath, wherein a first distal elongate element and a second distal elongate element of the at least two distal motion constraining elements intersect to form a cross-shape at the lateral side of the flexible sheath at the distal portion, the cross-shape of the first distal elongate element and the second distal elongate element corresponding to an axis of rotation of the distal interphalangeal joint intersecting the flexible sheath when the protective device is worn on the human finger, wherein a first proximal elongate element and a second proximal elongate element of the at least two proximal motion constraining elements intersect to form a cross-shape at the lateral side of the flexible sheath at the proximal portion, the cross-shape of the first proximal elongate element and the second proximal elongate element corresponding to an axis of rotation of the proximal interphalangeal joint intersecting the flexible sheath when the protective device is worn on the human finger, the protective device further comprising a further elongate element that extends from a position on the lateral side of the flexible sheath corresponding to a position of a shaft of the first phalanx when the flexible sheath is worn on the human finger to a position on the lateral side of the flexible sheath corresponding to a position of a shaft of the second phalanx when the flexible sheath is worn on the human finger.

2. The protective device of claim 1, wherein said flexible sheath is a structure for enveloping the human finger in a close-fitting manner, such as to exert a compressive force on the human finger when said flexible sheath is worn around said human finger.

3. The protective device of claim 1, wherein at least two of said at least two proximal motion constraining elements respectively cover each lateral side of the flexible sheath at opposite lateral locations of said proximal portion of the flexible sheath, and wherein at least two of said at least two distal motion constraining elements respectively cover each lateral side of the flexible sheath at opposite lateral locations of said distal portion of the flexible sheath.

4. The protective device of claim 1, wherein the flexible sheath defines a central portion between the proximal portion and the distal portion of the flexible sheath, wherein each of the at least two distal motion constraining elements and each of the at least two proximal motion constraining elements is secured to the flexible sheath in the central portion of the flexible sheath corresponding to said position of the shaft of said first phalanx when said flexible sheath is worn around said human finger and wherein each of the at least two distal motion constraining elements is further secured to the flexible sheath in the distal portion of the flexible sheath corresponding to said position of the shaft of said second phalanx, when the flexible sheath is worn around said human finger.

5. The protective device of claim 4, wherein the flexible sheath comprises a first annular elastic structure in the proximal portion and a second annular elastic structure in the distal portion for exerting a compressive force corresponding to the shaft of respectively said first phalanx and said second phalanx, when worn around said human finger, and wherein each of the at least two proximal motion constraining elements are secured to the first annular elastic structure and each of the at least two distal motion constraining elements are secured to the second annular elastic structure.

6. The protective device of claim 1, wherein an angle between the first distal elongate element and the second distal elongate element in the cross-shape of the first distal elongate element and the second distal elongate element is in a range of 10° to 40°, and wherein an angle between the first proximal elongate element and the second proximal elongate element in the cross-shape of the first proximal elongate element and the second proximal elongate element is in a range of 10° to 40°.

7. The protective device of claim 1, wherein the first distal elongate element of said at least two distal motion constraining elements extends from a position on the palmar side of the flexible sheath corresponding to a position of the shaft corresponding to the first phalanx when the flexible sheath is worn on the human finger to a position on the dorsal side of the flexible sheath corresponding to a position of the shaft corresponding to the second phalanx when the flexible sheath is worn on the human finger, and wherein the second distal elongate element of the two distal motion constraining elements extends from a position on the dorsal side of the flexible sheath corresponding to the position of the shaft corresponding to the first phalanx when the flexible sheath is worn on the human finger to a position on the palmar side of the flexible sheath corresponding to the position of the shaft corresponding to the second phalanx, when the flexible sheath is worn on the human finger.

8. The protective device of claim 1, wherein said flexible sheath comprises at least one opening for exposing a dorsal aspect of the proximal and/or distal interphalangeal joint, when the flexible sheath is worn on the human finger.

9. The protective device of claim 1, wherein said flexible sheath comprises an opening for exposing a fingertip of said human finger when said flexible sheath is worn on said human finger.

10. The protective device of claim 1, further comprising a plurality of flexible sheaths including said flexible sheath, each of said plurality of flexible sheaths comprising a base, wherein said bases of the plurality of flexible sheaths are joined together to form a connective textile of a glove for wearing on a human hand, said connective textile covering at least a proximal part of a proximal phalanx of said human hand when the glove is worn.

11. The protective device of claim 10, wherein said glove comprises a wristband for enclosing a wrist of said human hand when worn, wherein said connective textile connects to the wristband across a first lateral side of the glove, the first lateral side of the glove corresponding to an ulnar side of the human hand when the glove is worn on the human hand and wherein said connective textile connects to the wristband across a second lateral side of the glove, the second lateral side of the glove corresponding to a radial side of said human hand and a base of a thumb of said human hand when the glove is worn on the human hand.

12. The protective device of claim 11, wherein said glove comprises a strap for connecting the connective textile at the second lateral side of the glove to the connective textile at the first lateral side of the glove, such as to leave an opening between said strap and the bases of the plurality of flexible sheaths, the opening between the strap and the bases of the plurality of flexible sheaths corresponding to dorsal aspects of the metacarpophalangeal joints of said human hand when said glove is worn.

13. The protective device of claim 10, wherein said connective textile comprises a gusset connecting a terminal flexible sheath from the plurality of flexible sheaths to a further one of the plurality of flexible sheaths, the terminal flexible sheath corresponding to a thumb of said human hand when worn and the further one of the plurality of flexible sheaths corresponding to a forefinger of said human hand when worn, wherein said gusset is configured to stretch to a taut condition at a predetermined extension between the terminal flexible sheath and the further one of the plurality of flexible sheaths, said predetermined extension corresponding to a full extension between the thumb of the human hand and the forefinger of the human hand when worn.

\* \* \* \* \*